United States Patent [19]

Menger

[11] Patent Number: 4,826,769
[45] Date of Patent: May 2, 1989

[54] BIOCHEMICALLY REACTING SUBSTRATES IN SUBTERRANEAN CAVITIES

[75] Inventor: William M. Menger, Houston, Tex.
[73] Assignee: Houston Industries Incorporated, Houston, Tex.
[21] Appl. No.: 693,028
[22] Filed: Jan. 22, 1985
[51] Int. Cl.$^4$ ............................................... C12P 5/02
[52] U.S. Cl. ..................................... 435/167; 210/603; 210/630; 48/210; 585/943
[58] Field of Search ............... 435/167; 210/603, 630; 48/210; 585/943

[56] References Cited

U.S. PATENT DOCUMENTS

| | | | |
|---|---|---|---|
| 3,185,216 | 5/1965 | Hitzman | 166/42 |
| 3,665,716 | 5/1972 | Rogers et al. | 61/35 |
| 3,826,308 | 7/1974 | Compere-Whitn | 166/246 |
| 3,858,397 | 1/1975 | Jacoby | 61/0.5 |
| 4,140,423 | 2/1979 | Boulanger | 405/53 |
| 4,323,367 | 4/1982 | Ghosh | 48/197 A |
| 4,356,269 | 10/1982 | Thomsen et al. | 435/316 |
| 4,518,399 | 5/1985 | Croskell et al. | 210/603 |

OTHER PUBLICATIONS

"Isolation and Description of Haloanaerobium Praevalens Gen. Nov. and Sp. Nov. an Obligately Anaerobic Halophile Common to Great Sale Lake Sediments", by J. G. Zeikus et al., Current Microbiology, vol. 9 (1983), pp. 225–234.
"Removal of Sulfur Compounds from Coal by the Thermophilic Organism Sulfolobus Acidocaldarius", by Fikret Kargi et al., Applied and Environmental Microbiology, Oct. 1982, pp. 878–883.
"Conference focuses on Microbial Enhancement of Oil Recovery", by Erle C. Donaldson Technology, Dec. 20, 1982, Oil & Gas Journal, pp. 47–52.
"Geothermal Deep Sea Marine Life Now Found in Shallow Water", by Sandra Blakeslee, New York Times, Jun. 8, 1984.
"Preliminary Design Study of Compressed Air Energy Storage in a Salt Dome", United Engineers & Constructors, Inc., EPRI EM-2210, vol. 3, Project 1081-2, Apr. 1982.

Primary Examiner—Charles F. Warren
Assistant Examiner—Carolyn Greason
Attorney, Agent, or Firm—Pravel, Gambrell, Hewitt, Kimball & Krieger

[57] ABSTRACT

A method for carrying out biochemical reaction is disclosed. The method includes placing a suitable substrate in a cavity formed in a subterranean formation, inoculating the substrate with a culture of microorganisms, maintaining conditions suitable for the growth of the microorganisms, allowing the microorganisms to grow in the substrate in the cavity, and recovering a biochemical product formed thereby. The method is especially suitable for the conversion of alkali-oxidized or hydrolyzed coal, such as lignite, to methane.

20 Claims, 1 Drawing Sheet

BIOCHEMICALLY REACTING SUBSTRATES IN SUBTERRANEAN CAVITIES

FIELD OF INVENTION

This invention relates to utilizing subterranean cavities formed for the purposes of biochemically reacting a substrate placed therein. More particularly, this invention relates to producing useful products by the growth of microorganisms in a substrate placed in a cavity formed in a subterranean salt formation, limestone, or other earthen rock or sandstone formations.

DESCRIPTION OF THE PRIOR ART

Many useful products have been obtained by the action of microbial organisms from the digestion of carbohydrates by microorganisms, such as ethanol, insulin by man-made microorganisms, and methane from the anaerobic digestion of biomass. Because of the slow growth or action of the microbes, it is often necessary to use a large reactor to produce biochemical products in usable quantities. Often, startup times ranging up to several months are required for the microbes to grow to achieve a sufficient population density in the substrate to produce usable quantities of the desired biochemical products. Further, conditions for the microorganisms, including temperature, pH and toxic substance concentrations, must be maintained within critical limits to avoid killing the microbes. Thus, if such conditions are not maintained, mortality of the microorganisms will result and the growth thereof must be reinitiated.

In the conversion of biomass to methane, the above problems are particularly acute because of the large volumes of biomass and methane involved. Much effort has been directed to providing suitable and economic reactors for the conversion of biomass into methane. For example, U.S. Pat. No. 4,356,269 described a semi-submerged insulated apparatus which has a preheating chamber provided with a heating device, a gas processing chamber in which the microorganisms are grown, and a storage chamber for spent manure.

The anaerobic digestion of biomass is typically a three-step process in which complex organic materials are converted to the end products of methane and carbon dioxide. In the initial steps, complex organic molecules are converted into organic acids such as propionate, butyrate, valerate, lactate, formate and ethanol, and eventually into acetate. The organisms responsible for this conversion are collectively termed acid formers and may be either anaerobic or facultative in nature. The final step, the conversion of acetate to methane and carbon dioxide is performed by organisms collectively termed methane formers, or methanogens, which are strictly anaerobic. Because the methanogens generally grow more slowly than do the acid formers, the final step of the process is considered the rate limiting step. Generally, conversion of a complex organic substrate yields a gas which is typically sixty to seventy percent methane and thirty to forty percent carbon dioxide.

Reactor environmental parameters of concern for providing proper anaerobic digestion conditions include temperature, pH, alkalinity, volatile acid concentrations, nutrients, and toxic substances. These environmental parameters must be controlled within specific ranges for adequate digestion to occur, especially due to the sensitivity and slow growth of methane formers.

Three general temperature ranges exist for anaerobic fermentation, psychrophilic (10° to 20° C.), mesophilic (30° to 40° C.), and thermophilic (50° to 60° C.). Generally, anaerobic digesters are operated in the mesophilic or thermophilic temperature ranges because of the higher digestion rates. In the anaerobic digesters heretofore known, heat is carefully supplied to maintain the appropriate temperature. If the temperature is too low, the digestion rate is unsatisfactory. On the other hand, if the temperature is too high, the microorganisms may be killed. Only in systems operating in the phychrophilic range with extremely high microbial densities are the digester operated without supplying heat thereto.

The pH, alkalinity and volatile acid concentrations are interdependent. For stable anaerobic digestion to occur, the system pH should be between 6.6 and 7.6, with an optimum range of 7.0 to 7.2. Volatile acids, an intermediate product in the fermentation process, can increase in concentration if a system imbalance occurs due to other environmental factors which inhibit the growth of the methane formers. In such a situation, volatile acid concentrations will increase and the pH will drop, thus further aggravating the situation until the digester fails completely. Typically, this problem is avoided by properly buffering the digester with alkali to a near neutral pH.

A variety of organic and inorganic substances are required for adequate digestion to occur, including carbon, nitrogen, phosphorous, sulfur, vitamins and trace minerals. Organic materials deficient in one or more of these nutrients are typically supplemented. Generally, a weight ratio of carbon to nitrogen to phosphorous of 100:5:1 is adequate.

Numerous substances, if present in a high enough concentration, will pose inhibitory or toxicity problems in a digester. The substances of major concern include sulfdies (greater than 200 mg/l), soluble heavy metals (greater than 1.0 mg/l), alkaline earth metals such as sodium (5000–8000 mg/l), potassium (4000–10,000 mg/l), calcium (2000–6000 mg/l), and magnesium (1200–3500 mg/l), and ammonia (1700–4000 mg/l).

Conventional anaerobic digesters are of four classes. Completely mixed, single stage anaerobic digesters are the most common form of reactors used to stabilize organic materials and produce methane gas. These reactors have been used in treating municipal sewage, industrial waste, and agricultural residues. Generally, completely mixed digesters are maintained at a constant volume by feeding and withdrawing the same volume of influent and effluent. These digesters are agitated on an intermittent or continuous basis depending upon the specific material being digested and have a relatively long retention time of ten to thirty days. This system is typically used with residues having organic concentrations in excess of 10,000 mg/l of biological oxygen demand (BOD).

Although in theory this type of system can operate on a more dilute waste, the economics of conversion are unfavorable. Because of the long retention times and slow rate of substrate conversion, dilute wastes are not converted rapidly enough or to the degree necessary to produce enough methane to sustain the process. Moreover, the start up period required to achieve efficient steady state operation of a competely mixed, single stage anaerobic digester may be as long as a few months or more, depending upon the quantity of seed material initially placed in the digester and the retention time at which the system is operated.

Another type of digester, the anaerobic contact process, is a modification of the completely mixed, single stage anaerobic digester. As with the completely mixed, single stage anaerobic digester, the anaerobic contact process is operated in such a manner as to maintain a constant volume by adding substrate thereto and withdrawing effluent therefrom at equivolume rates. The effluent is fed to a clarifier in which biological solids are settled, withdrawn and recirculated into the digester. Some of the recycled solids are periodically removed from the system so that inert solids will not accumulate. The clarified liquid overflows from the clarifier and is discharged. In this manner, the hydraulic retention time of the digester can be minimized to less than a day while biological solids are retained in the system for significantly longer periods, ten days or more. Consequently, dilute concentrations of organic wastes can be converted to methane and carbon dioxide quickly in a reactor which is comparatively small with respect to the single stage system. The viability of the anaerobic contact process is dependent on the ability of the clarifier to separate the biological solids from the liquid to produce a low volume, highly concentrated recycled stream. Because the biological settling characteristics are substrate dependent, the system is not readily adaptable to a wide variety of substrates.

Another type of digester is the plug flow anaerobic digester in which the feed entering the reactor passes through the reactor as a discrete plug and each plug leaves the reactor in the same sequence in which it entered. Theoretically, each plug remains in the reactor for a period of time equal to the theoretical retention time and no internal mixing occurs. As each plug moves through the reactor, the microbial concentration will increase as the substrate concentration decreases. Hence, each plug of material can be considered a batch reactor travelling through the plug flow digester with time. Since the residue to be digested does not normally contain organisms required for digestion, each plug of feed will require inoculation with the required microbe. This inoculum is provided by recycling effluent solids from the effluent end of the digester back to the influent stream. Typically, as with the anaerobic contact process, clarification and solids recycle is employed.

Theoretically, in ideal plug flow, back mixing, sedimentation and flotation of solids and shortcircuiting do not occur. However, in practice, ideal plug flow conditions are impossible to maintain. Plug flow conditions are approximated by providing a long, narrow, horizontal reactor and using a substrate which is viscous to inhibit particulate settlement or flotation and which has a high concentration of solids. With this type of waste, clarification may be impossible. Typically, hydraulic retention times are on the order of ten to thirty days or more. As with the other systems, plug flow digesters require long start up times.

Yet another digester is the anaerobic packed bed digester which includes an elongated, vertical unit packed with an inert biological support medium such as gravel, raschig rings, berl saddles or the like. The liquid waste is introduced into the bottom of the reactor and removed from the top. The packing material provides a support or attachment surface for the anaerobic microbes. Hence, high concentrations of organisms can be maintained in the reactor, allowing for rapid conversion at lower temperatures. Because the organisms are attached to a fixed surface and occur in significantly higher concentrations than in other types of reactors, the units are highly stable and will recover from toxic or hydraulic shock more readily than other systems. Generally, packed bed digesters are operated with hydraulic retention times of six hours to three days depending upon the substrate. Solids retention times will be significantly longer, up to 100 days or more, because the solids remain trapped in the bed and are not generally carried over with the effluent.

Other digesters which are exemplary of attempts to avoid the aforenoted problems include the in situ conversion of biomass reactants. For example, in U.S. Pat. No. 3,826,308 there is described a process in which a naturally occurring fossil fuel deposit is contacted in situ with an anaerobic fermenting microorganism. A more soluble intermediate product is formed which may be converted into organic acids by another microorganism. Yet another microorganism converted the organic acids into valuable products.

Another approach to in-situ recovery of petroleum from underground deposits utilizing microorganisms was that of U.S. Pat. No. 3,185,216. A well was drilled through adjacent petroleum bearing and water bearing formations, inoculating the water bearing formation with a microorganism which grows at the oil-water interface to release the petroleum, and then plugging back above the water formation after inoculation.

Similarly, U.S. Pat. No. 4,323,367 describes a process for improved gas production and accelerated stabilization of landfills by in situ bioleaching of organic waste acid-forming bacteria. The leachate is acted on by microorganisms in an acid phase digester. Part of the acid phase digester effluent is recirculated to the landfill to supply additional microorganisms and the remainder is used to produce methane from a methane phase digester.

It has also been known that caverns formed in subterranean salt domes, whether naturally occurring or otherwise formed, could be used for storing various materials, such as solid wastes (U.S. Pat. No. 3,665,716) and liquified gases (U.S. Pat. No. 4,140,423). Bacteria were introduced into the solid waste storage dome cavern to assist in refuse decomposition. U.S. Pat. No. 3,858,397 related to the use of cavern salt domes to take advantage of their heat conducting characteristics for conducting heat promotable chemical reactions. Heat from the earth core was conducted by the salt dome to caverns. The cavern or caverns were located at depths where temperatures greater than the boiling point of water were present. At times, substantially higher temperatures, such as 200° C. to 250° C., were preferred. The thermal properties and conditions of salt dome caverns discouraged their consideration for use as vessels for biochemical reactions.

SUMMARY OF THE INVENTION

With the present invention, the aforementioned problems of prior art digesters are avoided by the growth of microorganisms under controlled temperature and pressure conditions in a substrate placed in a subterranean cavern or salt formation.

Briefly, the present invention is a method for carrying out a biochemical reaction which includes the steps of: placing a substrate suitable for the growth of microorganisms in a cavity formed in a subterranean cavern or salt formation; introducing a culture of microorganisms into the substrate; controlling conditions in the cavity to promote the growth of the microorganisms in the substrate; allowing the microorganisms to grow in the substrate in the cavity; and, recovering a biochemical product from the cavity which is formed by the growth of the microorganisms in the substrate in the cavity.

The method of the present invention broadly contemplates the production of useful products by the growth of microorganisms, those naturally occurring as well as genetically altered microbes, in suitable substrates. The method is particularly adaptable to microbially mediated biochemical reactions which require relatively large reactors to produce useable quantities of the desired products, such as the conversion of a substrate, typically coal in an aqueous alkali slurry enriched with nitrogen and phosphorous nutrients, to methane by anaerobic microorganisms. Preferably, the substrate to be converted has a weight ratio of nitrogen to carbon of at least 5:100, and of phosphorus to carbon of at least 1:100. Preferably, the microorganisms used to convert the substrate into methane include both acid formers and methanogens and the conditions of the substrate in the cavity include a pH between about 3 and about 10 and a temperature below about 100° C. for most known methanogenic bacteria (but up to 225° C. for some thermophiles). The products formed by the acid formers and methanogens in the substrate at such conditions are primarily methane, carbon dioxide and organic acids.

DETAILED DESCRIPTION OF THE PREFERRED EMBODIMENT

Figure 1:
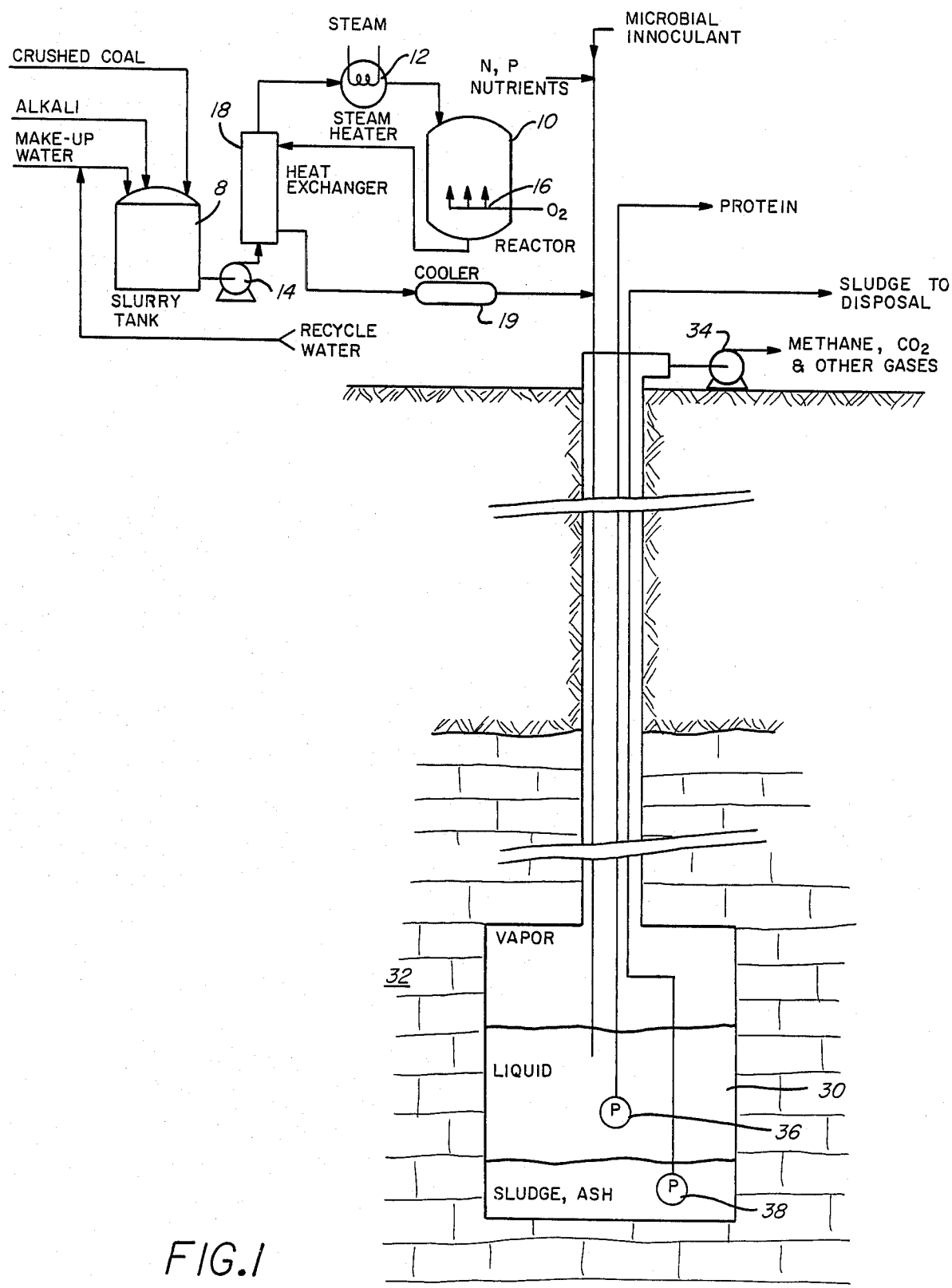
FIG. 1 is a schematic illustration of the method of the present invention in which coal is converted into methane and carbon dioxide in a cavity formed in a subterranean formation.

The method may be carried out in a naturally occurring subterranean cavity or in a cavity formed in a subterranean salt formation by well-known methods, such as solution mining. Because most microbially mediated biochemical reactions require moderate temperatures to sustain the microorganisms, it is preferred that the subterranean cavity be located at a shallow enough depth where the naturally occurring temperature coincides with the optimum temperature for the selected strain of microbes in order that the temperature of the substrate in the cavity can be maintained without cooling. Although in the preferred embodiment the subterranean cavity is in a subterranean salt dome, the method of the present invention may also be performed in solution mined limestone caverns as well as caverns which are physically mined in limestone, granite or other geological locations.

Suitable substrates in the method of the invention include solutions or pumpable suspensions of any organic material which satisfies the proper nutrient requirements for the microorganisms to be employed. It is also essential that the concentration in the substrate of substances toxic to the microorganims to be employed remain sufficiently low to avoid mortality of the microorganisms. If the organic material to be used in the substrate is deficient in one or more nutrients, it may be rendered suitable for use as a substrate by the addition thereto of the appropriate nutrients. Likewise, it may be possible to remove toxic substances from a material to the extent that it is suitable for use as a substrate.

Depending on the conditions maintained in the substrate in the cavity, the use of virtually any known microorganism, naturally occurring or man-made by being genetically altered under laboratory conditions, is contemplated in the invention. For use in salt domes ,the microoganisms must, of course, be salt tolerant. It may in some instances, however, not be possible to maintian the necessary conditions to sustain certain microorganisms in specific substrates and/or liquid media. For example, microorganisms which are sensitive to salt are not suitable for use in the invention if the salt concentration in the substrate or liquid medium is allowed to exceed lethal levels by the dissolving of salt from the walls of the cavity into the substrate. In some instances, however, this problem may be avoided by reducing the residence time of the substrate in the cavity, by reducing the solubility of salt in the liquid medium employed such as, for example, by maintaining a lower temperature or by addition thereto a nontoxic substance which reduces the solubility of the salt therein, or by use of a liquid medium in which salt is not soluble. In many cases, it is believed that it will be within the capability of those skilled in the art to select or develop microorganisms which are relatively insensitive to salt. For example, it has been reported that certain cultures are capable of reducing sulfates and producing methane from carbon dioxide in salt marshes. Also, salt-tolerant anaerobic microbes have been recovered by Professor Zeikus (University of Wisconsin) from sediments in the Great Salt Lake, Utah. See, e.g., the article by Zeikus et al., "Isolation and Description of Haloanaerobriem prevalens gen. nov. and sp. nov., an obligately anaerobic halophile common to Great Salt Lake Sediments." Current microbiology, Vol. 9, pp. 225-234 (1983). There appear to be other known sources of bacterial cultures to develop a community of organisms to accomplish coal gasification. They include sewage sludge bacteria, bacteria from areas such as Yellowstone Park which are tolerant of high temperatures and accustomed to a diet of substances including carbon and sulfur (Kargi et al., "Removal of Sulfur Compounds from Coal by the Thermophilic Organism: Sulfolobus Acidocaldarius", Applied and Environmental Microbiology, Vol. 44, pp. 878-883, Oct. 1982); methane producing bacteria found naturally in petroleum formations at depths of from 5,000 to 20,000 feet and deeper, which can be collected from drilling mud at drilling rigs (Donaldson et al., "Conference Focuses on Microbial Enhancement of Oil Recovery", Oil and Gas Journal, Vol. 80, pp. 47-52, Dec. 20, 1982); and bacterial cultures or ecosystems found in fumaroles being investigated by the National Oceanographic Laboratory at La Jolla, California ("Geothermal Deep Sea Marine Life Now Found in Shallow Water", New York Times, June, 1984). In an illustrative embodiment described below, the temperature and pH ranges given are for one particular range of organisms insensitive to salt used in a subterranean salt cavity. The conditions described apply to conventional microorganisms which have evolved at or near the earth's surface at conditions similar to those present in the subterranean salt cavity. Depending on the organism selected, other cavities, temperature and pH ranges, and cavity depths could be used.

The substrate is placed in the subterranean cavity by appropriate means, including pumping or gravity flow, through a pipe or other suitable conduit communicating between the cavity and the surface. In the case of solid, insoluble organic material, the substrate may be placed in the cavity in the form of a liquid suspension. A culture of the microorganisms may be introduced into the substrate prior to the placing thereof in the cavity. Alternatively, the inoculation may be accomplished by introducing the microbes directly into the cavity. Once the substrate and microorganisms are in place in the cavity, conditions in the substrate in the cavity which are suitable for promoting the growth of the microorganisms are controlled. If necessary, the substrate may be heated or cooled by circulation of the substrate from the cavity, heating or cooling the substrate at the surface and returning the heated or cooled substrate to the cavity. Alternatively, a heating or cooling medium may be circulated from the surface into the cavity in indirect heat exchange with the substrate and back to the surface. Preferably, the cavity is located at the proper depth to provide the optimum temperature without heating or cooling. The pH of the substrate and the cavity may be controlled by periodic or continuous addition thereto of appropriate acids, bases or buffers. Similarly, the nutrients in the substrate may be supplemented by a periodic or continuous addition of deficient nutrients thereto. Likewise, the concentration of toxic substances in the substrate may be controlled by continuous or periodic addition thereto of neutralizing agents or by continuous or periodic removal of the substrate or biochemical products resulting from the growth or action of the microorganisms in the substrate. For example, where the growth of the microorganisms in a liquid substrate results in the formation of insoluble products, sediment may be removed from the lower portion of the cavity by means of a submerged sludge pump.

After the microorganisms and substrate have been in the cavity for a sufficient length of time at the proper conditions, biochemical products which are formed by the growth of the microorganisms in the substrate in the cavity are recovered. The product may be in the form of a gas, miscible or immiscible liquid, or soluble or insoluble solid, or a combination of these forms. Gas is removed from the upper portion of the cavity by means of a fan or compressor. Liquid or solid products are removed by pumping from appropriate depths in the cavity.

In an especially preferred embodiment of the invention, a substrate is anaerobically converted into methane. Preferably, the source of the substrate is coal. With the present invention, coal is used in the sense of carbonized vegetable material including peat, lignite, subbituminous coal, bituminous coal and anthracite coal. Lignite is the preferred substance due to its wide availability and its unsuitability for use in place of higher rank coal for certain purposes. Structurally, lignite is characterized by relatively low aromaticity, approximately 60% aromatic. The aromatic clusters of lignite are primarily one and two rings in contrast to bituminous coals having fused ring systems of 3 or more aromatics. In addition, lignite is characterized by a prevalance of oxygen-functional groups such as carboxylate, phenolic and ethereal components. Lignite also contains moisture and ash. The ash-containing portion of lignite contains both inorganics, such as calcium and sodium ions, and minerals, such as clay, pyrite and quartz. While the ash and moisture content may vary among lignites, the variation in the organic portion is not significant. As used herein, the term "lignite volatile solids" (LVS) refers to the organic portion of the lignite.

To render it suitable for use in the substrate, lignite is contacted in a finely divided state, i.e., substantially all particles less than about one-quarter inch, with a hot aqueous alkali solution and with or without oxygen in alkali hydrolysis vessel or reactor 10 as seen in FIG. 1. The crushed coal and alkali are mixed wtih water in a slurry prep tank 8 prior to heating and injection into the reactor 10 at elevated pressures. A temperature of from about 150° C. to about 300° C., preferably 200° C. to 250° C., is maintained in vessel 10 by preheating the feed to the reactor through heater 12. Pump 14 provides the pressure for the reaction.

The alkali used is not particularly critical and examples include potassium hydroxide, sodium hydroxide or sodium carbonate. The alkali is added to the crushed coal at a rate of from about 0.2 to about 20% on an LVS weight basis.

Oxygen can be introduced into vessel 10 by means of sparger 16 or other suitable means. The source of oxygen is preferably air, but may be purified oxygen. The amount of oxygen required is approximately 1 pound per pound LVS. A portion of the heat required to heat the alkali solution and the lignite is provided by the oxidation of the lignite. It should also be understood that in some instances, oxygen need not be used in the pretreatment step. In these situations, no sparger 16 need be present in the vessel 10.

The alkali oxidation of the lignite may be performed as a batch operation, but is preferably a continuous operation. In a continuous operation in which vessel 10 is continuously stirred, a residence time of 1.5 hours will result in a conversion of approximately 83% of the organic portion of the lignite into low molecular weight organics. The concentration of the organics in the liquid effluent from vessel 10 may be as high as 20% by weight or more. Preferably, the organic concentration is at least about 15% by weight.

The alkali hydrolized lignite solution is then cooled to lower the temperature down to about 35°-55° C. which is the preferred temperature for conducting the fermentation of the organics into methane. Cooling is performed in heat exchanger 18 preferably by heat exchange with the feed to vessel 10 and/or by cooling water in cooler 19. If desired, undissolved solids may be removed by filtration prior to anaerobic digestion. Alternatively, the solids may be removed from cavity 30 as a sludge which accumulates in the lower portion thereof.

Because lignite is normally deficient in nitrogen and phosphorus, these nutrients are added to the organic solution. Suitable nutrient supplements include potash and urea in amounts sufficient to result in a weight ratio of nitrogen to carbon in the organic solution (typically) of about 5:100, and of phosphorus to carbon of about 1:100.

The microbial inoculant includes acid formers and methanogens. The acid formers convert large organic molecules such as proteins, starches, and celulose into organic acids and are anaerobic and/or facultative in nature. The metanogens convert the organic acids into methane and carbon dioxide and are strictly anaerobic. The microorganisms may be either psychrophilic, mesophilic or thermophilic.

The inoculated organic fluid solution or mixture is fed via an influent pipe into cavity 30 formed in salt formation 32. The location of solution injection is preferably near the bottom of the cavity 30, but a suitable distance above bottom to allow room for ash and microbial sludge to accumulate. This is done in order to avoid physical removal of these solids during the service life of the cavern. If desired, a packed bed of crushed stone may be deposited on the cavity bottom to provide greater chemical reactant surface.

Conditions in the substrate are maintained such that the growth of the microorganisms therein is promoted. The temperature is maintained from about 10° C. to about 60° C., preferably 10°-20° C. for psychrophilic microorganisms, 30°-40° C. for mesophilic and 50°-60° C. for thermophilic. If necessary, the organic solution or mixture in the cavity may be heated or cooled as described above. The pH is maintained between about 6.5 and about 8.5, preferably between 6.6 and 7.6, and most preferably between 7.0 and 7.2. The pH may be continuously or periodically adjusted by addition to the organic solution or mixture of acids or bases. However, buffering the organic solution or mixture with alkali at a near neutral pH will normally control the pH.

When the process of the present invention is performed in subterranean salt caverns, the biogasification reaction is preferably carried out in an aqueous broth containing greater than a 10% concentration of sodium chloride. Microbes are known to operate under anaerobic conditions at concentrations of 10-20% sodium chloride. The use of broths with less than 10% sodium chloride requires special precautions to avoid or minimize leaching of sodium chloride from the cavern walls.

The microorganisms in the inoculated organic fluid solution or mixture are allowed to grow in the cavity for a sufficient period of time to convert a significant quantity of the organics into methane. The length of time required may range from 1 day to approximately 30 days, depending on the desired conversion rate and the specific substrate and conditions in the cavity. Methane and carbon dioxide are recovered from a vapor space at the top of the cavity through an effluent pipe by means of fan 34. The effluent and influent pipes should be on opposite sides of the cavity 30 so that the reacting liquid can be recirculated. The recovered gaseous mixture of methane and carbon dioxide may be subsequently processed to recover purified methane and carbon dioxide according to conventional processing methods. A protein-rich broth is recovered by means of broth pump 36. The protein may subsequently be recovered and used for chemical feedstocks. Sediment may be removed from the cavity by means of sludge pump 38 or left in the cavity itself as an economical disposal alternative. The sludge contains insoluble lignite and/or solids formed by the growth of the microbes in the organic solution or mixture. The sludge can be disposed of or burned for fuel. A recirculation valve 40 is provided in the protein recovery line for recirculating the broth from broth pump 36, if desired.

While my method is illustrated in the foregoing description, many variations in the size, shape and materials, as well as in the details of the illustrated method, will occur to those skilled in the art. It is intended that all such variations which fall within the scope and spirit of the appended claims be embraced thereby.

I claim:

1. A method for carrying out a biochemical reaction in a cavity in a subterranean formation, comprising the steps of:
    (a) treating a substrate of carbonized vegetable material by contacting it in a finely divided state with a hot aqueous alkali solution to produce low molecular weight organics;
    (b) introducing the substrate from the surface into the cavity in the subterranean formation;
    (c) introducing a culture of anaerobic microorganisms into the substrate in the cavity;
    (d) controlling conditions in the substrate in the cavity to those suitable for promoting growth of the microorganisms;
    (e) allowing the microorganisms to grow in the substrate in the cavity and form a biochemical product,
    (f) recovering from the cavity the biochemical product formed by growth of the microorganisms.

2. The method of claim 1, wherein said step of introducing a substrate comprises placing a substrate having a nitrogen to carbon ratio of at least about 5:100 and a phosphorus to carbon ratio of at least about 1:100.

3. The method of claim 1, wherein said step of introducing a culture of anaerobic microorganisms comprises the step of introducing acid formers.

4. The method of claim 1, wherein said step of controlling conditions is said cavity comprises maintaining a pH between about 6.5 and about 8.5 and a temperature between about 10° C. and about 60° C.

5. The method of claim 1, wherein the biochemical product is a gaseous mixture including methane and carbon dioxide.

6. The method of claim 1, wherein said step of controlling conditions in said cavity comprises maintaining a pH between about 6.5 and about 8.5.

7. The method of claim 1, wherein said step of controlling conditions in said cavity comprises maintaining a temperature between about 10° C. and about 60° C.

8. The method of claim 1, wherein the anaerobic microorganisms are genetically altered.

9. The method of claim 1, wherein the anaerobic microorganisms are naturally occurring.

10. A method for biochemically converting coal to methane, comprising the steps of:
    (a) treating the coal by contacting the coal in a finely divided state with a hot aqueous alkali solution at a temperature of from about 150° C. to about 300° C. to produce an aqueous mixture of low molecular weight organics;
    (b) feeding the organic solution or mixture into a subterranean cavity;
    (c) inoculating the organic solution or mixture with a methanogenic microorganism culture;
    (d) maintaining the inoculated organic solution or mixture in the cavity at a pH between about 6.5 and about 8.5 and at a temperature between about 10° C. and about 60° C.;
    (e) allowing the microorganisms to grow in the organic solution or mixture in the cavity to produce methane; and
    (f) recovering the produced methane from the cavity.

11. The method of claim 10, further including the step of:
    adding nutrients to the aromatics solution in an amount sufficient to result in said solution having a nitrogen to carbon weight ratio of at least 5 to 100 and a phosphorus to carbon weight ratio of at least 1 to 100.

12. The method of claim 10, further including the step of:
    cooling the aromatics solution to a temperature less than about 60° C. prior to said step of inoculating.

13. The method of claim 10, further including the step of purifying the produced methane.

14. The method of claim 10, wherein a microorganism-rich broth is also formed during said step of allowing the microorganism to grow and further including the step of:

recovering the broth from the cavity.

15. The method of claim 10, wherein a sludge is a microorganism-rich broth is also formed during said step of allowing the microorganisms to grow and further including the step of:

removing the sludge from the cavity.

16. The method of claim 10, further including the step of:

simultaneously contacting the coal in the finely divided state with oxygen during said step of treating.

17. The method of claim 10, wherein:

said step of treating is performed in the absence of oxygen.

18. The method of claim 10, wherein:

the aqueous mixture produced during said step of treating has a molecular weight of less than 500.

19. The method of claim 10, wherein the anaerobic microorganisms are genetically altered.

20. The method of claim 10, wherein the anaerobic microorganisms are naturally occurring.

* * * * *

UNITED STATES PATENT AND TRADEMARK OFFICE
CERTIFICATE OF CORRECTION

PATENT NO. : 4,826,769
DATED : May 2, 1989
INVENTOR(S) : William M. Menger

It is certified that error appears in the above-identified patent and that said Letters Patent is hereby corrected as shown below:

Column 1, line 37, delete "described" and insert --describes--

Column 2, line 11, delete "digester" and insert --digesters--
Column 2, line 39, delete "and" before "magnesium"

Column 3, line 31, delete "The oretically" and insert --Theoretically--
Column 3, line 32, delete "the oretical" and insert --theoretical--
Column 3, line 45, delete "Ther oretically" and insert --Theoretically--

Column 4, line 19, delete "in-situ" and insert --in situ--

Column 6, line 30, delete "microbiology" and insert --Microbiology-

Column 8, line 2, delete "wtih" and insert --with--

Column 10, line 19, delete "is" and insert --in--

Signed and Sealed this

Sixth Day of February, 1990

Attest:

JEFFREY M. SAMUELS

*Attesting Officer*     *Acting Commissioner of Patents and Trademarks*